(12) United States Patent
Takatori et al.

(10) Patent No.: US 11,511,067 B2
(45) Date of Patent: Nov. 29, 2022

(54) RESPIRATION ASSISTANCE DEVICE

(71) Applicant: NIHON KOHDEN CORPORATION, Tokyo (JP)

(72) Inventors: Fumihiko Takatori, Tokyo (JP); Kenichiro Kabumoto, Tokyo (JP); Masayuki Inoue, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 930 days.

(21) Appl. No.: 16/353,305

(22) Filed: Mar. 14, 2019

(65) Prior Publication Data

US 2019/0298956 A1 Oct. 3, 2019

(30) Foreign Application Priority Data

Mar. 27, 2018 (JP) .............................. JP2018-059667

(51) Int. Cl.
*A61M 16/06* (2006.01)
*A61B 90/16* (2016.01)
(Continued)

(52) U.S. Cl.
CPC ........... *A61M 16/0666* (2013.01); *A61B 1/24* (2013.01); *A61B 5/082* (2013.01); *A61B 5/097* (2013.01);
(Continued)

(58) Field of Classification Search
CPC .............. A61M 16/0666; A61M 16/06; A61M 16/0003; A61M 16/0488; A61M 16/049; A61M 16/0493; A61M 16/0497; A61M 16/0672; A61M 16/0677; A61M 16/085; A61M 2202/0208; A61M 2202/0225;
(Continued)

(56) References Cited

U.S. PATENT DOCUMENTS 5,273,032 A * 12/1993 Borody ............. A61M 16/0493
128/207.14
5,335,656 A 8/1994 Bowe et al.
(Continued)

FOREIGN PATENT DOCUMENTS

EP 2 196 236 A1 6/2010
JP H03-500496 A 2/1991
(Continued)

OTHER PUBLICATIONS

Japanese Office Action dated Nov. 30, 2021 issued in Japanese Patent Application No. 2018-059667.
(Continued)

*Primary Examiner* — Colin W Stuart
(74) *Attorney, Agent, or Firm* — Pearne & Gordon LLP

(57) ABSTRACT

A respiration assistance device includes a nasal respiration assisting section for supplying a gas to the nasal cavity of a living body. The nasal respiration assisting section includes: a first gas supplying portion which supplies a gas below one of the nostrils of the living body; a second gas supplying portion which supplies the gas below the other nostril of the living body; a first tube connecting portion to which a tube for supplying the gas to the first gas supplying portion is connectable; and a second tube connecting portion to which a tube for supplying the gas to the second gas supplying portion is connectable.

8 Claims, 9 Drawing Sheets

(51) Int. Cl.
*A61B 1/24* (2006.01)
*A61M 16/04* (2006.01)
*A61M 16/08* (2006.01)
*A61B 5/08* (2006.01)
*A61B 5/00* (2006.01)
*A61B 5/097* (2006.01)
*A61B 1/015* (2006.01)
*A61B 1/00* (2006.01)

(52) U.S. Cl.
CPC ............ *A61B 5/6819* (2013.01); *A61B 90/16* (2016.02); *A61M 16/0493* (2014.02); *A61M 16/0672* (2014.02); *A61M 16/085* (2014.02); *A61M 16/0816* (2013.01); *A61B 1/00154* (2013.01); *A61B 1/015* (2013.01); *A61M 2202/0208* (2013.01); *A61M 2202/0225* (2013.01); *A61M 2205/3306* (2013.01); *A61M 2230/432* (2013.01)

(58) Field of Classification Search
CPC ...... A61M 2202/3306; A61M 2230/40; A61M 2230/43; A61M 2230/432; A61B 90/16; A61B 1/24; A61B 1/00154; A61B 5/097; A61B 5/6819
See application file for complete search history.

(56) References Cited

U.S. PATENT DOCUMENTS

| | | | |
|---|---|---|---|
| 5,513,634 A | 5/1996 | Jackson | |
| 6,422,240 B1 | 7/2002 | Levitsky et al. | |
| 2004/0015092 A1 | 1/2004 | Pettersson | |
| 2006/0278238 A1* | 12/2006 | Borody | A61B 1/24 128/859 |
| 2007/0068535 A1 | 3/2007 | Colman et al. | |
| 2008/0110456 A1* | 5/2008 | Flynn | A61M 16/0488 128/200.26 |
| 2008/0295849 A1* | 12/2008 | Reynolds, II | A61M 16/0493 128/200.26 |
| 2009/0275851 A1* | 11/2009 | Colman | A61B 1/2736 128/205.24 |
| 2010/0198096 A1 | 8/2010 | Colman et al. | |
| 2010/0262033 A1 | 10/2010 | Colman et al. | |
| 2010/0317987 A1 | 12/2010 | Inoue et al. | |
| 2012/0125332 A1* | 5/2012 | Niland | A61M 16/00 128/207.18 |
| 2014/0039339 A1 | 2/2014 | Colman et al. | |
| 2014/0116447 A1 | 5/2014 | Cortez, Jr. et al. | |
| 2016/0022129 A1 | 1/2016 | Colman et al. | |
| 2017/0333656 A1 | 11/2017 | Colman et al. | |

FOREIGN PATENT DOCUMENTS

| | | |
|---|---|---|
| JP | 2003-533322 A | 11/2003 |
| JP | 2007-500566 A | 1/2007 |
| JP | 2010-136869 A | 6/2010 |
| WO | 89-09565 A1 | 10/1989 |
| WO | 2015-049538 A1 | 4/2015 |
| WO | 2017-217264 A1 | 12/2017 |

OTHER PUBLICATIONS

Partial European Search Report issued in European Patent Application No. EP 19 16 2698 dated Jul. 23, 2019.

Extended European Search Report issued in Patent Application No. EP 19 16 2698 dated Sep. 26, 2019.

* cited by examiner

RESPIRATION ASSISTANCE DEVICE

CROSS-REFERENCE TO RELATED APPLICATIONS

This application is based on and claims priority under 35 USC 119 from Japanese Patent Application No. 2018-059667 filed on Mar. 27, 2018, the contents of which are incorporated herein by reference.

TECHNICAL FIELD

The presently disclosed subject matter relates to a respiration assistance device.

BACKGROUND ART

When an endoscopic surgical procedure is performed through the oral cavity or the nasal cavity, there is a case where an analgesic anesthesia is applied to the living body in order to mitigate the pain of the living body under the procedure. In the case where an endoscopic surgical procedure is performed with using an analgesic anesthesia, a respiration assistance device for supplying a treatment gas (hereinafter, referred to simply as "gas") such as an oxygen gas to the oral cavity or the nasal cavity is used in order to prevent respiratory arrest from occurring as a side effect.

An example of such a respiration assistance device is a respiration assistance device which is to be attached to the periphery or below the nostrils in order to supply a gas to the nasal cavity, and which assists the nasal respiration. Another example of a respiration assistance device is a device having a function of supplying a gas to a bite block which, in the case where an endoscopic surgical procedure is performed through the oral cavity, is attached to the oral cavity so that the living body does not bite the endoscope. In some respiration assistance devices, a sensor for measuring the concentration of carbon dioxide contained in the expiration (hereinafter, such a sensor is referred to as "$CO_2$ sensor") can be attached to the living body in order to monitor the respiratory condition of the living body.

As a technique relating to a respiration assistance device, a bite block is disclosed which may be used with separate oral/nasal cannulae, or which may incorporate breath sampling or gas supply cannulae (for example, see Patent Literature 1).

CITATION LIST

Patent Literature

Patent Literature 1: JP-T-2007-500566

SUMMARY OF INVENTION

It is often that an analgesic anesthesia which is performed in a surgical procedure continues for several hours even after the surgical procedure is ended. Also after the surgical procedure, therefore, the gas supply using a respiration assistance device, and the monitoring of the respiratory condition by a $CO_2$ sensor which is attached to the respiration assistance device are continued for a predetermined time period. After the surgical procedure, as a respiration assistance device, only a respiration assistance device for assisting the nasal respiration is used.

Conventionally, for example, a respiration assistance device which is provided with a function of assisting the nasal respiration, and which has a bite block is used during a surgical procedure, and, after the surgical procedure, the respiration assistance device is replaced with a respiration assistance device for the nasal respiration. In some of conventional respiration assistance devices, a respiration assistance device for the nasal respiration, and a bite block can be separated from each other. In the case where the bite block is detached from the oral cavity, and only the respiration assistance device for the nasal respiration is used, a tube for supplying a gas to the bite block is not used. Conventionally, therefore, it is necessary to perform, after the surgical procedure, bothersome works of detaching the respiration assistance device, and of detaching the bite block and the tube for supplying a gas to the bite block.

In another conventional respiration assistance device, a one-way valve is attached to a tube for a bite block, and, after the bite block is detached, the valve prevents a gas from leaking. In the respiration assistance device, however, a bothersome work of fixing the tube must be performed after the bite block is detached. Since the one-way valve is disposed, moreover, the cost of the respiration assistance device is increased.

It is an object of the presently disclosed subject matter to improve the convenience of a respiration assistance device when the device is used.

The presently disclosed subject matter provides a respiration assistance device which includes a nasal respiration assisting section for supplying a gas to a nasal cavity of a living body, wherein the nasal respiration assisting section includes: a first gas supplying portion which supplies the gas below one of nostrils of the living body; a second gas supplying portion which supplies the gas below another nostril of the living body; a first tube connecting portion to which a tube for supplying the gas to the first gas supplying portion is connectable; and a second tube connecting portion to which a tube for supplying the gas to the second gas supplying portion is connectable.

According to the presently disclosed subject matter, it is possible to improve the convenience of a respiration assistance device when the device is used.

DESCRIPTION OF EMBODIMENTS

Hereinafter, an embodiment of the respiration assistance device of the presently disclosed subject matter will be described with reference to the drawings. In the embodiment, when a surgical procedure is performed with using an endoscope which is inserted through the oral cavity or nasal cavity of the human body that is an example of the living body, the respiration assistance device supplies a gas to the oral cavity and the nasal cavity. In the embodiment, the respiration assistance device which will be described is a device to which a $CO_2$ gas sensor (hereinafter, also referred to simply as "gas sensor") is attached in order to monitor the respiratory condition of the human body. The gas sensor measures the concentration of carbon dioxide contained in the expiration, as an example of the predetermined gas component with using a light emitting element and a light detecting element.

[Configuration of Respiration Assistance Device]

Figure 1:
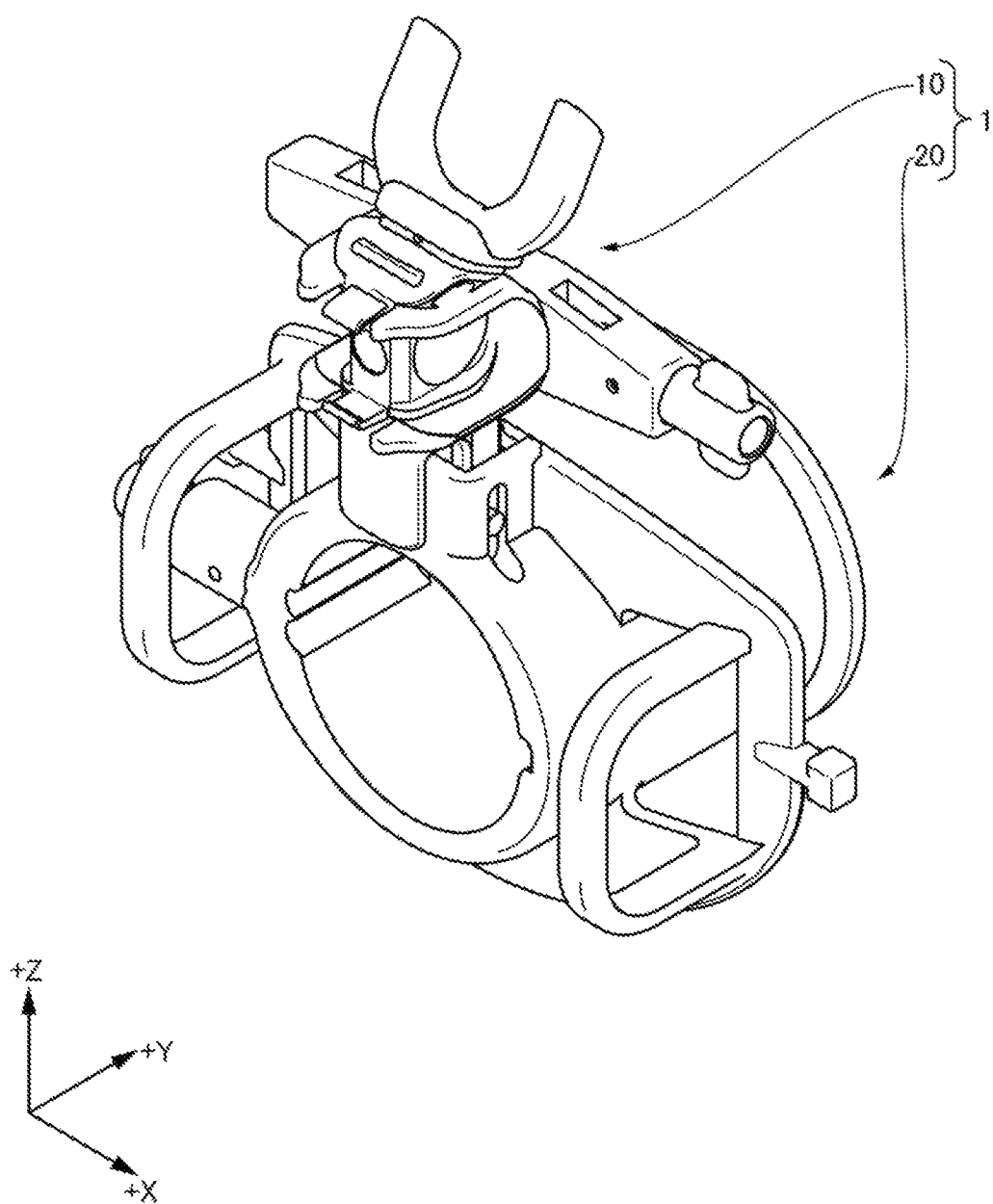
FIG. 1 is a perspective view illustrating an embodiment of the respiration assistance device of the presently disclosed subject matter.

FIG. 1 is a perspective view illustrating an embodiment of the respiration assistance device 1 of the presently disclosed subject matter. As illustrated in FIG. 1, the respiration assistance device 1 may include a nasal respiration assisting section 10 and a bite block 20.

In the following description and the drawings, it is assumed that the direction which, when the respiration assistance device 1 is attached to the human body that is an example the living body, is opposed to the face of the human body is the front direction. In the following description and the drawings, directions as seen in the front direction in the case where the respiration assistance device 1 is attached to the human body are assumed as follows: the left direction as viewed toward the face of the human body to which the respiration assistance device 1 is attached is the −X direction; the right direction as viewed toward the face is the +X direction; the direction which is directed toward the interior of the oral cavity of the human body is the +Y direction; the direction which is separated from the oral cavity of the human body is the −Y direction; the direction which is directed toward the upper side (the vertex) of the face of the human body is the +Z direction; and the direction which is directed toward the lower side (the jaw) is the −Z direction.

The nasal respiration assisting section 10 is attached below the nostrils of the human body. The nasal respiration assisting section 10 supplies the gas to the nasal cavity of the human body through the nostrils.

The bite block 20 is attached to the oral cavity of the human body in order to suppress the movement of the mouth in the open mouth state so that the living body does not bite an endoscope or the like which is inserted into the oral cavity. The nasal respiration assisting section 10 and the bite block 20 will be described later in detail.

[Configuration of Nasal Respiration Assisting Section]

Figure 2:
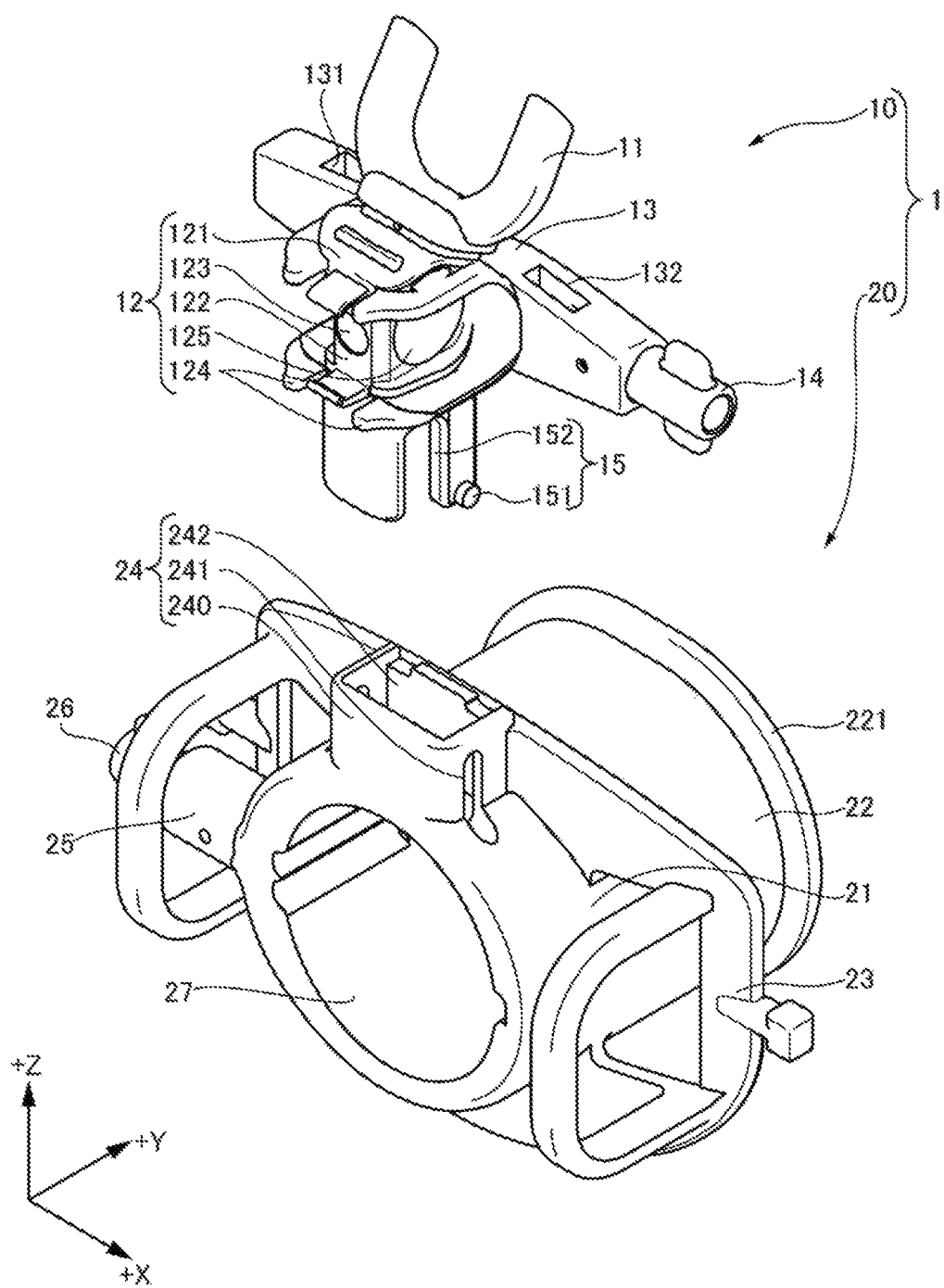
FIG. 2 is a perspective view illustrating a state where a nasal respiration assisting section and bite block of the respiration assistance device illustrated in FIG. 1 are separated from each other.
Figure 3:
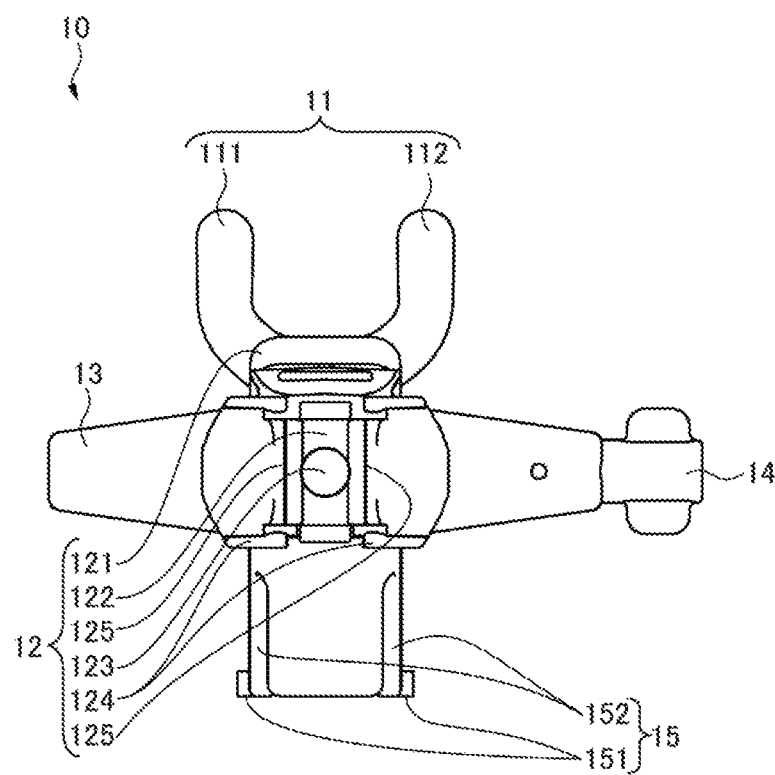
FIG. 3 is a front view illustrating the nasal respiration assisting section of the respiration assistance device illustrated in FIG. 1.
Figure 3:
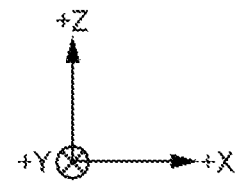

FIG. 2 is a perspective view illustrating a state where the nasal respiration assisting section 10 and bite block 20 of the respiration assistance device 1 are separated from each other, and FIG. 3 is a front view illustrating the nasal respiration assisting section 10 of the respiration assistance device 1. The configuration of the nasal respiration assisting section 10 will be described with reference to FIGS. 2 and 3.

As illustrated in FIG. 2, the nasal respiration assisting section 10 may include a nasal cavity expiration introducing portion 11, a gas sensor attaching portion 12, a gas supplying portion 13, a tube connecting coupler 14, and a first fitting portion 15.

In the nasal respiration assisting section 10, when the position where the gas sensor attaching portion 12 is disposed is set as the center, the nasal cavity expiration introducing portion 11 extends in the +Z and +Y directions. As illustrated in FIG. 3, in the upper part of the gas sensor attaching portion 12, the nasal cavity expiration introducing portion 11 branches off into a first nasal cavity expiration introducing portion 111 and a second nasal cavity expiration introducing portion 112.

Each of the first and second nasal cavity expiration introducing portions 111, 112 is configured by a fluid path having an approximately cylindrical shape. When the respiration assistance device 1 is attached to the human body, tip end portions of the first and second nasal cavity expiration introducing portions 111, 112 are inserted into the two nostrils of the human body, respectively. The nasal cavity expiration introducing portion 11 introduces the expiration which is emitted from the nasal cavity of the human body, toward the gas sensor attaching portion 12.

The gas sensor attaching portion 12 is disposed below the nasal cavity expiration introducing portion 11 in the −Z direction. The gas sensor attaching portion 12 may include a base portion 121, a gas sensor engaging portion 122, a magnet portion 123, a gas sensor locking portion 124, and a gas sensor measurement window 125. A gas sensor which is not illustrated can be attached to the gas sensor attaching portion 12.

The base portion 121 supports the nasal cavity expiration introducing portion 11 which is disposed on the gas sensor attaching portion 12.

The gas sensor engaging portion 122 is disposed so as to be engaged with the gas sensor. The gas sensor engaging portion 122 has a shape with which an engaged portion of the gas sensor can be engaged. Specifically, the gas sensor engaging portion 122 has a wall part in each of the front surface and the both side surfaces, thereby forming a space in the portion.

The magnet portion 123 can be contacted with a magnet portion which is disposed in the engaged portion of the gas sensor. The magnet portion 123 is disposed in, for example, the front-oriented surface of the gas sensor engaging portion 122. The magnet portion 123 is contacted with the magnet portion of the gas sensor to prevent the gas sensor from slipping off.

The gas sensor locking portion 124 has a shape which, in order to allow locking with at least a part of the housing of the gas sensor, can receive a part of the housing of the gas sensor.

The gas sensor measurement window 125 is a window in which, for example, a predetermined light transmittance is ensured. The gas sensor measurement window 125 is formed so that, when the gas sensor is attached, light emitted from the emitter of the gas sensor, and light propagating to the detector can pass through the window. The gas sensor measurement window 125 is disposed at a position which, when the gas sensor is attached, corresponds to the positions of the emitter and the detector.

Figure 4:
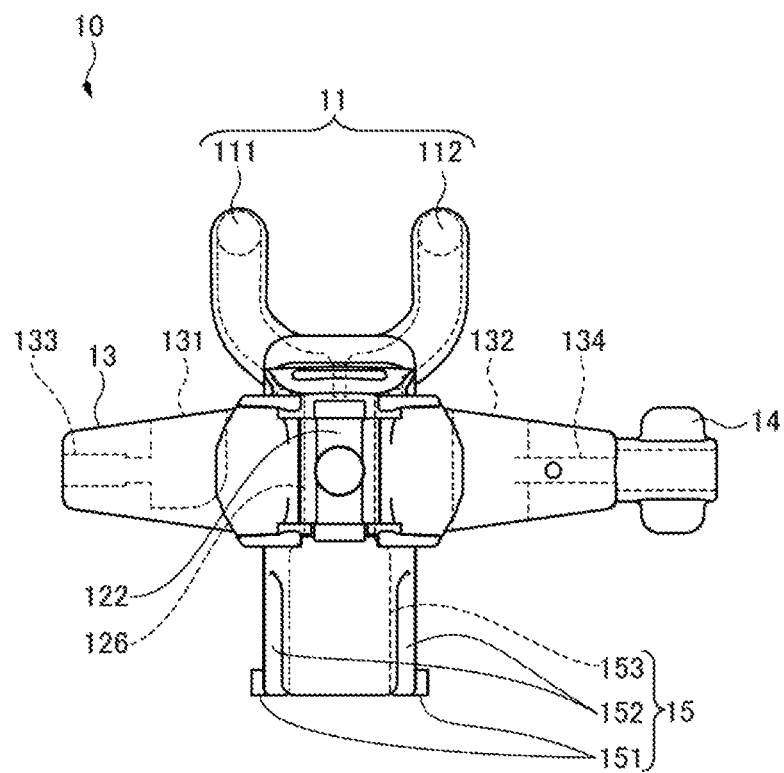
FIG. 4 is a diagram illustrating the internal structure of the nasal respiration assisting section illustrated in FIG. 2.
Figure 4:
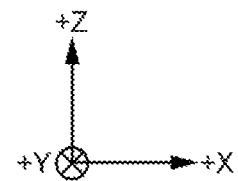

FIG. 4 is a diagram illustrating the internal structure of the nasal respiration assisting section 10. As illustrated in FIG. 4, an expiration collecting portion 126 is configured by the above-described space disposed inside the wall parts of the gas sensor engaging portion 122. The expiration collecting portion 126 collects the expiration which is introduced from the nasal cavity expiration introducing portion 11 and the oral cavity. The expiration collected by the expiration collecting portion 126 is subjected to measurement of the concentration of $CO_2$ by the gas sensor which is attached to the gas sensor engaging portion 122.

The gas supplying portion 13 is disposed so as to extend in the ±X directions with setting the position where the gas sensor attaching portion 12 of the nasal respiration assisting section 10 is disposed, as the center. As illustrated in FIGS. 2 and 4, the gas supplying portion 13 may include a first gas supplying portion 131, a second gas supplying portion 132, a first tube connecting portion 133, and a second tube connecting portion 134.

The first gas supplying portion 131 is configured by an opening of the fluid path for supplying the gas below one of the nostrils of the human body. The first gas supplying portion 131 is disposed on the left side as viewed in the direction toward the face of the human body, and supplies the gas toward the right nostril of the human body.

The second gas supplying portion 132 is configured by an opening of the fluid path for supplying the gas below the other nostril of the human body. The second gas supplying portion 132 is disposed on the right side as viewed in the direction toward the face of the human body, and supplies the gas toward the left nostril of the human body.

The first tube connecting portion 133 is disposed in an end part of the gas supplying portion 13 which is on the left side as viewed in the direction toward the face of the human body. The tube which is used for supplying the gas, and which is not illustrated can be connected to the first tube connecting portion 133. The tube which is connected to the first tube connecting portion 133 is bonded to the portion, and therefore undetachable from the portion. The first tube connecting portion 133 is configured by an opening which communicates with the first gas supplying portion 131. The gas which is supplied through the tube connected to the first tube connecting portion 133 is further supplied from the first gas supplying portion 131 to the nasal cavity through the right nostril of the living body.

The second tube connecting portion 134 is disposed in an end part of the gas supplying portion 13 which is on the right side as viewed in the direction toward the face of the human body. In the same or similar manner as the first tube connecting portion 133, the tube which is used for supplying the gas, and which is not illustrated can be connected to the second tube connecting portion 134. The tube which is connected to the second tube connecting portion 134 is detachable from the portion. The second tube connecting portion 134 is configured by an opening which communicates with the second gas supplying portion 132. The gas which is supplied through the tube connected to the second tube connecting portion 134 is further supplied from the second gas supplying portion 132 to the nasal cavity through the left nostril of the human body. As illustrated in FIG. 4, the first gas supplying portion 131 communicates only with the first tube connecting portion 133, and the second gas supplying portion 132 communicates only with the second tube connecting portion 134. That is, the fluid path for the gas which reaches the right nostril of the human body from the first tube connecting portion 133 through the first gas supplying portion 131, and that for the gas which reaches the left nostril of the human body from the second tube connecting portion 134 through the second gas supplying portion 132 are independent from each other.

The tube connecting coupler 14 is a coupler which is used for connecting the tube to the second tube connecting portion 134. Although, in FIGS. 1 to 4, the tube connecting coupler 14 is connected only to the second tube connecting portion 134, the embodiment is not limited to this. Namely, the tube connecting coupler 14 may be connected to the first tube connecting portion 133.

The first fitting portion 15 is disposed so as to extend in the −Z directions with setting the position where the gas sensor attaching portion 12 of the nasal respiration assisting section 10 is disposed, as the center. The first fitting portion 15 has an approximately box-like shape. The first fitting portion 15 may include engagement pins 151, first engagement grooves 152, and a first oral cavity expiration introducing portion 153.

The engagement pins 151 are disposed on the both side surfaces of the first fitting portion 15, respectively. The engagement pins 151 are configured by projections which extend in the ±X directions from the side surfaces of the first fitting portion 15, respectively.

The first engagement grooves 152 are disposed on the both side surfaces of the first fitting portion 15, respectively. The first engagement grooves 152 are configured by longitudinal notches which are formed in the +Z direction from the lower ends of the both side surfaces of the first fitting portion 15, respectively.

The first oral cavity expiration introducing portion 153 is configured by a fluid path which is formed inside a wall surface portion that forms the first fitting portion 15. The first oral cavity expiration introducing portion 153 communicates with the expiration collecting portion 126. The first oral cavity expiration introducing portion 153 introduces the expiration which is introduced from the oral cavity of the human body and the side of the bite block 20, to the expiration collecting portion 126.

[Configuration of Bite Block]

Figure 5:
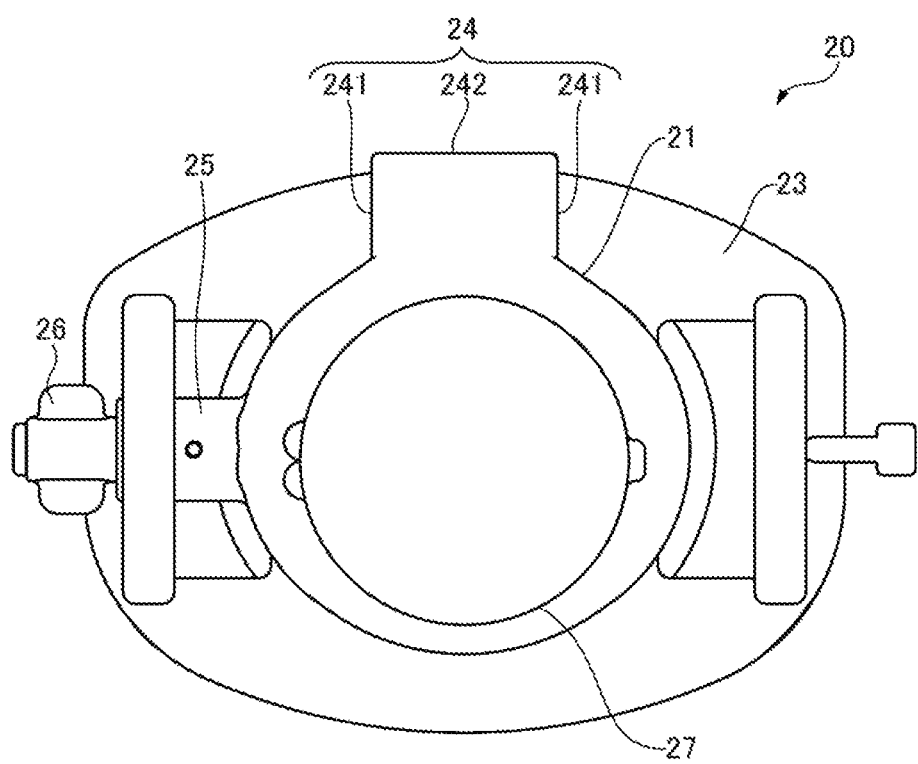
FIG. 5 is a front view illustrating the bite block of the respiration assistance device illustrated in FIG. 1.
Figure 6:
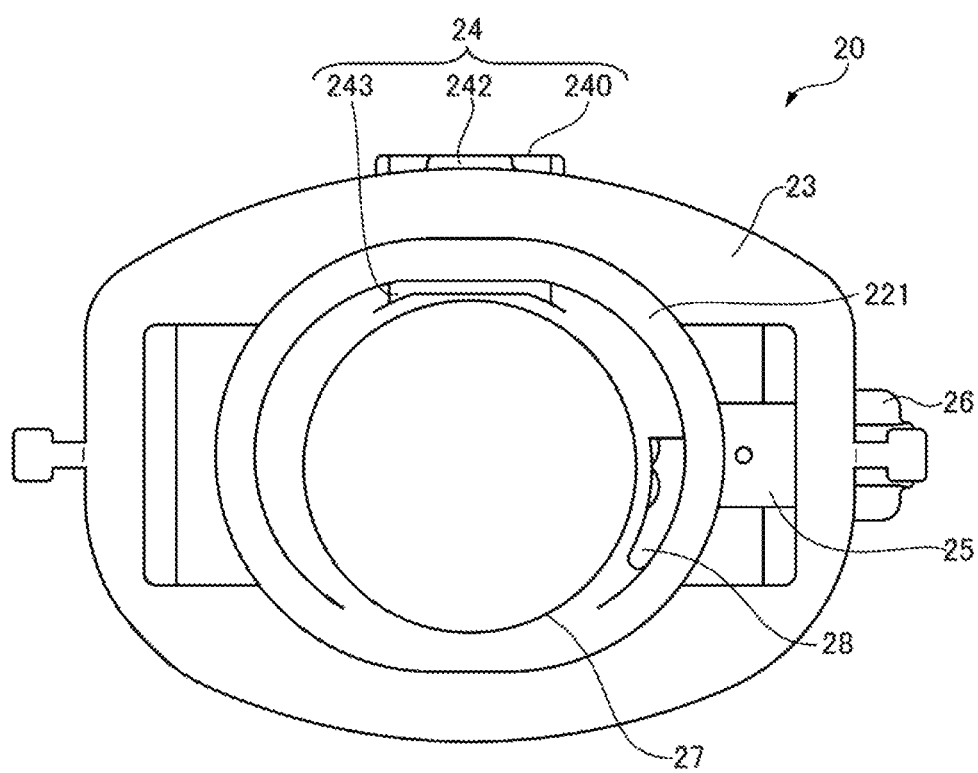
FIG. 6 is a back view illustrating the bite block illustrated in FIG. 5.
Figure 6:
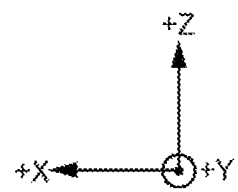

FIG. 5 is a front view illustrating the bite block 20 of the respiration assistance device 1, and FIG. 6 is a back view illustrating the bite block 20. As illustrated in FIGS. 2, 5, and 6, the bite block 20 may include a wall surface portion 21, an oral cavity contacting portion 22, a plate portion 23, a second fitting portion 24, a third tube connecting portion 25, a tube connecting coupler 26, a through hole 27, and a third gas supplying portion 28.

The wall surface portion 21 is formed into an approximately tubular shape in which the longitudinal direction coincides with the Y direction, and defines an approximate shape of the bite block 20. The oral cavity contacting portion 22 is disposed on the outer surface of the wall surface portion 21, and to be contacted with the oral cavity of the human body which is opened. The oral cavity contacting portion 22 suppresses the movement of the mouth in the open mouth state so that the human body does not bite an endoscope or the like which is inserted into the oral cavity. A rib 221 which, when the bite block 20 is attached to the human body, mitigates the contacting state in the oral cavity of the human body is disposed in the end portion of the oral cavity contacting portion 22 in the +Y direction.

The plate portion 23 is configured by an approximately planar member which intersects with the longitudinal direction of the wall surface portion 21 and the oral cavity contacting portion 22, or in other words an approximately plate-like member which is formed substantially along the XZ plane. The plate portion 23 is disposed in the Y-direction interface between the wall surface portion 21 and the oral cavity contacting portion 22. When the bite block 20 is attached to the human body, the plate portion 23 performs positioning with respect to the human body.

The second fitting portion 24 is configured by a member which extends from the upper surface of the wall surface portion 21 in the +Z direction. As illustrated in FIGS. 2, 5, and 6, the second fitting portion 24 may include a second fitting portion body 240, second engagement grooves 241, a second oral cavity expiration introducing portion 242, and an oral cavity expiration introducing opening 243.

The second fitting portion body 240 defines an approximate shape of the second fitting portion 24. In order to be fitted with the first fitting portion 15, the second fitting portion body 240 has a gutter-like shape in which the upper and lower ends are opened.

The second engagement grooves 241 are disposed on the both side surfaces of the second fitting portion body 240, respectively. In order to be engaged with the engagement pins 151 of the first fitting portion 15 of the nasal respiration assisting section 10, the second engagement grooves 241 are disposed at positions where the grooves can be engaged with the engagement pins 151, respectively. When the first fitting portion 15 and the second fitting portion 24 are engaged with each other, the first engagement grooves 152 of the first fitting portion 15 pass between the front and rear surfaces on the side of the front surface of the second fitting portion body 240. The first fitting portion 15 and the second fitting portion 24 enable the nasal respiration assisting section 10 and the bite block 20 to be detachably attached to the respiration assistance device 1.

The second oral cavity expiration introducing portion 242 is formed inside the second fitting portion body 240 in which the upper portion is opened. In the state where the first fitting portion 15 of the nasal respiration assisting section 10, and the second fitting portion 24 of the bite block 20 are fitted to each other, the second oral cavity expiration introducing portion 242 communicates with the expiration collecting portion 126 of the nasal respiration assisting section 10. Therefore, the second oral cavity expiration introducing portion 242 can introduce the expiration from the oral cavity into the expiration collecting portion 126.

When the bite block 20 is viewed from the back as illustrated in FIG. 6, the oral cavity expiration introducing opening 243 is opened inside the through hole 27. The oral cavity expiration introducing opening 243 communicates with the second oral cavity expiration introducing portion 242. The oral cavity expiration introducing opening 243 can introduce the expiration which flows inside the through hole 27 from the oral cavity of the human body, into the second oral cavity expiration introducing portion 242.

The third tube connecting portion 25 is configured by an approximately tubular member which extends from the left side surface of the wall surface portion 21 in the -X direction. A tube which is not illustrated, and which supplies the gas can be connected to the third tube connecting portion 25 with using the tube connecting coupler 26.

The tube connecting coupler 26 is a coupler which, in the same or similar manner as the above-described tube connecting coupler 14, is used for connecting the tube to the third tube connecting portion 25. The tube connecting coupler 26 can be connected to the second tube connecting portion 134 and the third tube connecting portion 25.

Figure 7:
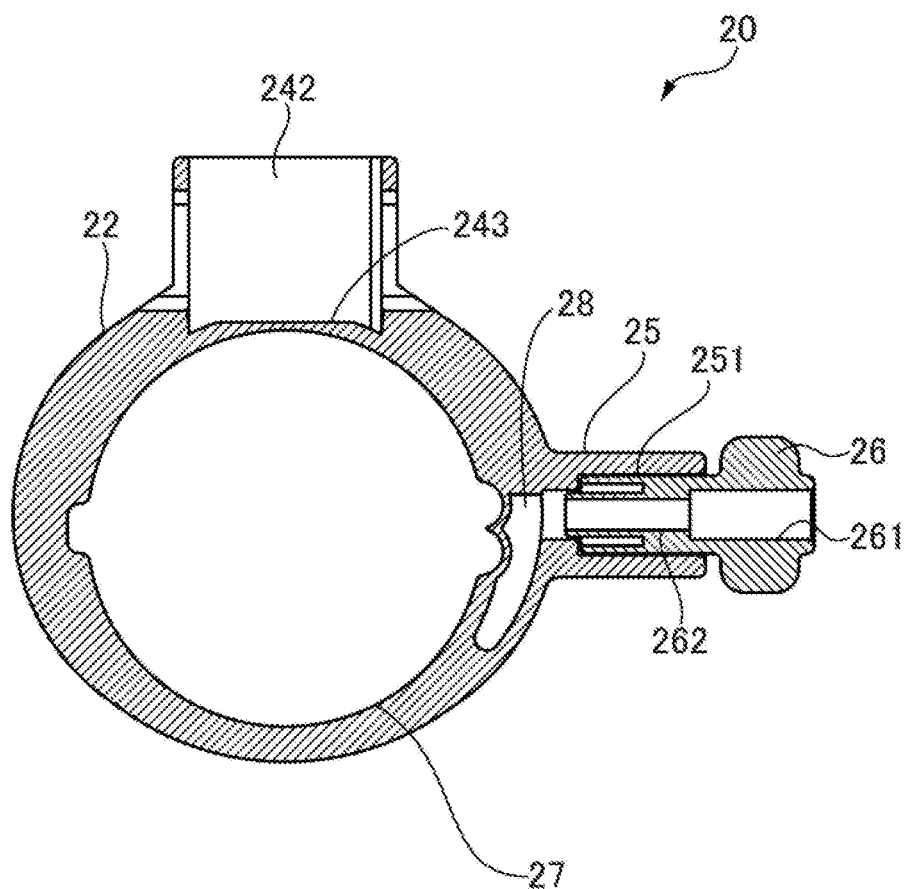
FIG. 7 is a section view of the bite block illustrated in FIG. 5, as seen from the back side.

FIG. 7 is a section view of the bite block 20, as seen from the back side. As illustrated in FIG. 7, the tube connecting coupler 26 may include a tube insertion hole 261 which is used for connecting the tube that is not illustrated, from the outside, and an intra-coupler fluid path 262 which communicates with the tube insertion hole 261. The tube connecting coupler 26 forms one fluid path through which the tube insertion hole 261 and the intra-coupler fluid path 262 communicate with each other. The third tube connecting portion 25 may internally include a pipe conduit 251 which communicates with the third gas supplying portion 28. The pipe conduit 251 has a shape which can receive a tip end portion of the tube connecting coupler 26.

The through hole 27 is disposed in the inner surface of the wall surface portion 21. The through hole 27 is disposed in order to enable a tubular article such as an endoscope to be inserted into the oral cavity.

The third gas supplying portion 28 is disposed in the through hole 27. The third gas supplying portion 28 communicates with the third tube connecting portion 25. Therefore, the gas which is supplied from the tube connecting coupler 26 that is connected to the third tube connecting portion 25 is supplied from the third gas supplying portion 28 to the oral cavity of the human body through the through hole 27.

[Use Example of Respiration Assistance Device]

Next, a use example of the respiration assistance device 1 which has been described above will be described.

Figure 8:
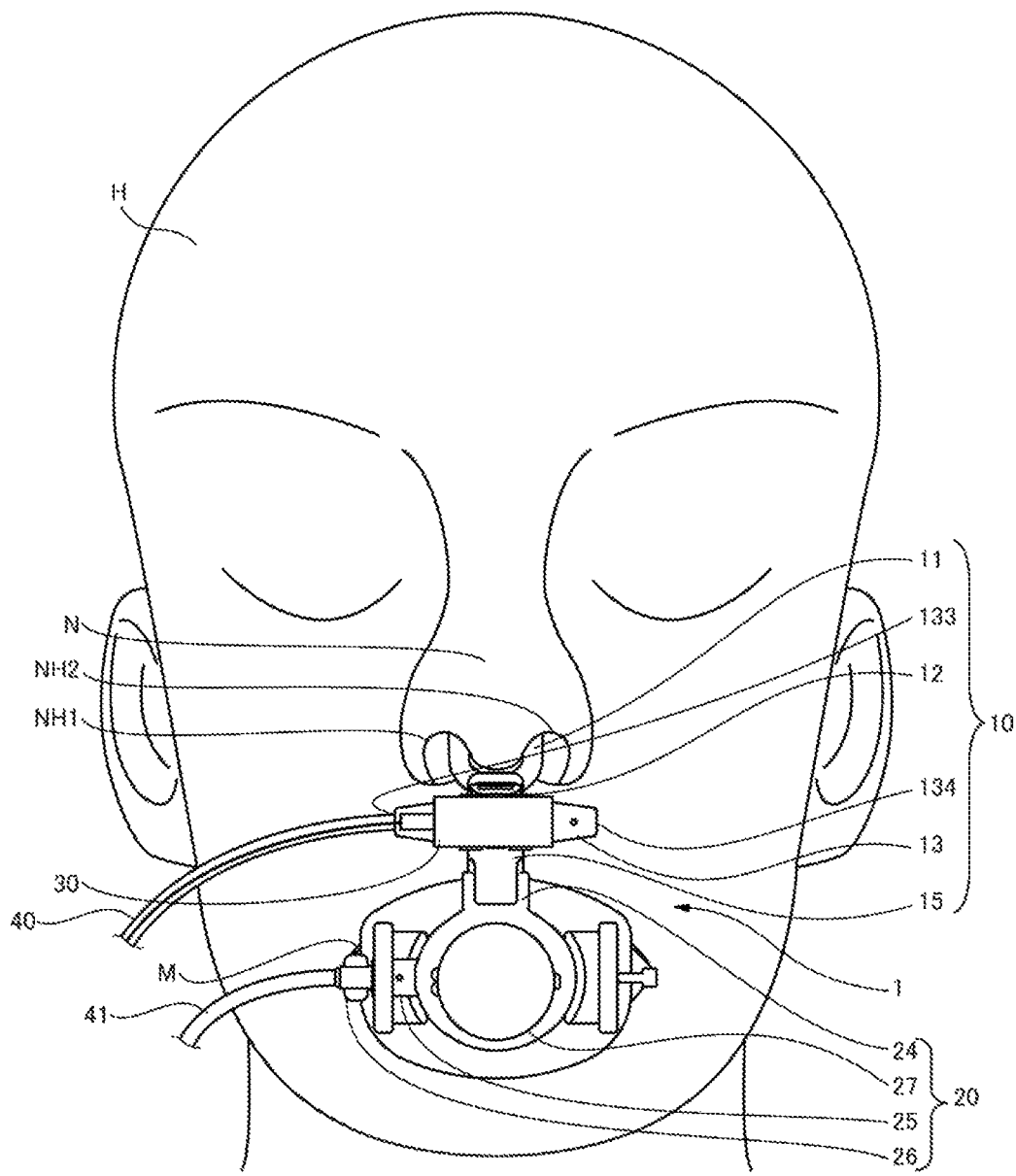
FIG. 8 is a diagram illustrating a state where the respiration assistance device illustrated in FIG. 1 is attached to the human body.

FIG. 8 is a diagram illustrating a state where the respiration assistance device 1 is attached to the human body H. FIG. 8 illustrates the state where the respiration assistance device 1 in which the nasal respiration assisting section 10 and the bite block 20 are integrated with each other is attached to the human body H. In order to monitor the respiratory condition of the human body H, a gas sensor 30 is attached to the gas sensor attaching portion 12 of the respiration assistance device 1.

As illustrated in FIG. 8, when the respiration assistance device 1 is attached to the human body H, the nasal cavity expiration introducing portion 11 of the nasal respiration assisting section 10 of the respiration assistance device is inserted into the nostrils NH1 and NH2 of the nose N. The gas supplying portion 13 of the nasal respiration assisting section 10 is placed below the nose N of the human body H. The bite block 20 of the respiration assistance device 1 is attached to the mouth M of the human body H.

In the case where the bite block 20 is attached to the nasal respiration assisting section 10, a tube 40 is connected to the first tube connecting portion 133 of the nasal respiration assisting section 10. The tube connecting coupler 26 is connected to the third tube connecting portion 25 of the bite block 20. A tube 41 is connected to the tube connecting coupler 26.

When the tube 40 is connected to the first tube connecting portion 133, the gas supplying portion 13 can supply the gas from the first gas supplying portion 131 illustrated in FIGS. 2 and 5 to the nostril NH1 of the human body H which is above the first gas supplying portion. When the tube connecting coupler 26 to which the tube 41 is connected is connected to the third tube connecting portion 25, the bite block 20 can supply the gas from the third gas supplying portion 28 to the oral cavity in the mouth M of the human body H.

The tube 40 may not be connected to the first tube connecting portion 133, but may be connected to the second tube connecting portion 134.

Figure 9:
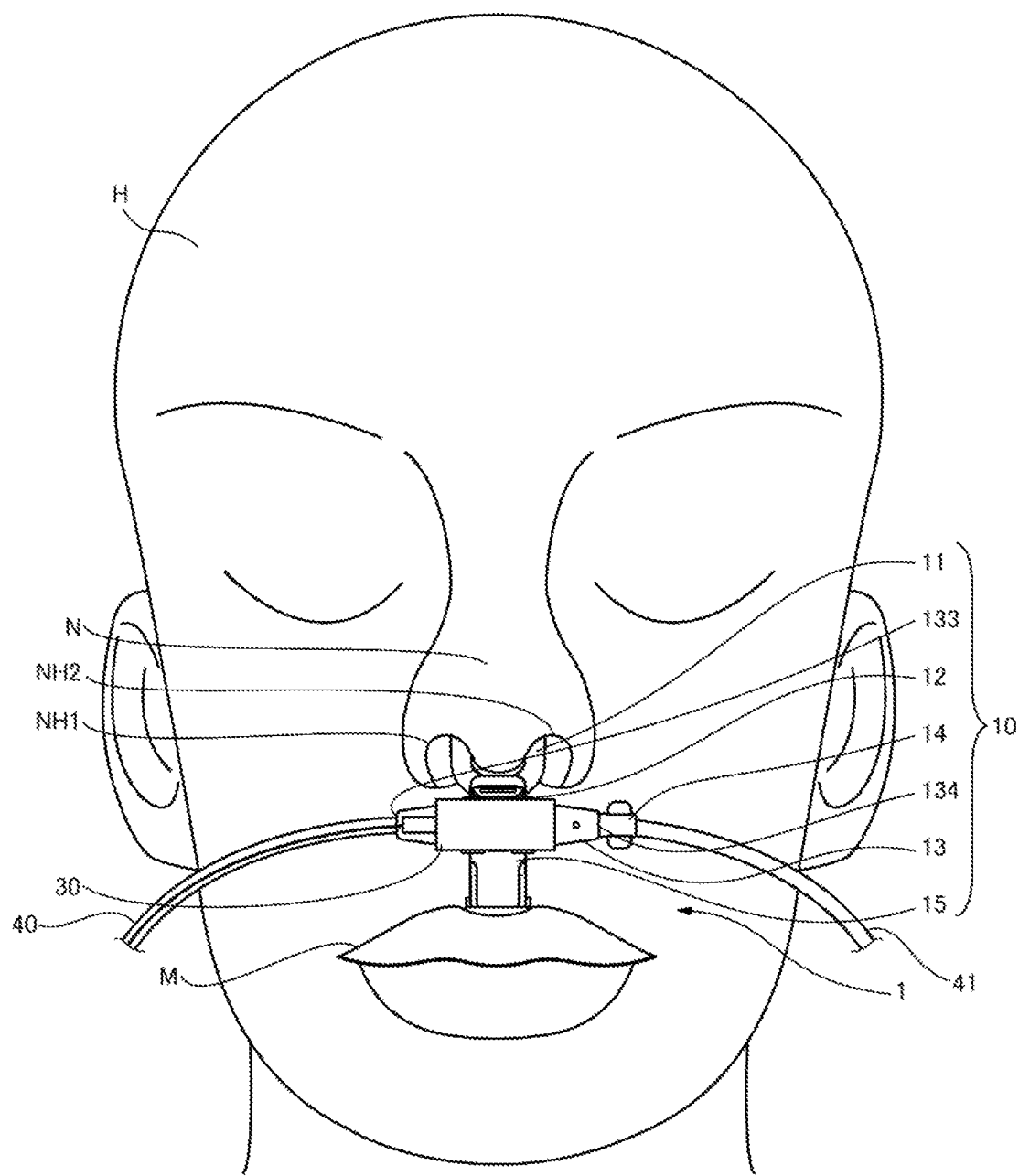
FIG. 9 is a diagram illustrating a state where the nasal respiration assisting section of the respiration assistance device illustrated in FIG. 1 is attached to the human body.

FIG. 9 is a diagram illustrating a state where the nasal respiration assisting section 10 of the respiration assistance device 1 is attached to the human body H. FIG. 9 illustrates the respiration assistance device 1 in the state the bite block 20 is detached from the respiration assistance device, and only the nasal respiration assisting section 10 is attached to the human body H. In the same or similar manner as FIG. 8, in order to monitor the respiratory condition of the human body H, the gas sensor 30 is attached to the gas sensor attaching portion 12 of the respiration assistance device 1.

In the case where the bite block 20 is detached from the respiration assistance device 1, in the nasal respiration assisting section 10, the tube 40 is connected to the first tube connecting portion 133, and in addition the tube connecting coupler 14 is connected to the second tube connecting portion 134. The tube connecting coupler 14 is obtained as a result of an operation in which the tube connecting coupler 26 that is connected to the third tube connecting portion 25 of the bite block 20 in FIG. 8 is detached in accordance with the detaching of the bite block 20, and then connected to the second tube connecting portion 134.

In addition to the tube 40, also the tube 41 is connected to the nasal respiration assisting section 10, specifically to the second tube connecting portion 134. According to the configuration, the gas supplying portion 13 can form a gas supply route from the first gas supplying portion 131 illustrated in FIGS. 2 and 5 to the nostril NH1, and in addition another gas supply route from the second gas supplying portion 132 to the nostril NH2.

In the respiration assistance device 1, as described above, the nasal respiration assisting section 10 includes: the first gas supplying portion 131 which supplies the gas below the one nostril of the living body; and the first tube connecting portion 133 which communicates with the first gas supplying portion 131, and to which the tube 40 or 41 for supplying the gas is connectable. The nasal respiration assisting section 10 further includes: the second gas supplying portion 132 which supplies the gas below the other nostril; and the second tube connecting portion which communicates with the second gas supplying portion 132, and to which the tube for supplying the gas is connectable. Here, the path which is formed by the first gas supplying portion 131 and the first tube connecting portion 133, and which extends from the nostril NH1 to the nasal cavity, and that which is formed by the second gas supplying portion 132 and the second tube connecting portion 134, and which extends from the nostril NH2 to the nasal cavity do not communicate with each other, and are independent from each other.

According to the respiration assistance device 1, in the case where, after a surgical procedure, for example, the device is used while detaching the bite block 20, therefore, the convenience in the use can be improved by reducing the trouble of replacing the respiration assistance device itself, and that of removing the tube for the bite block.

According to the respiration assistance device 1, the tube 41 which has been used for the bite block 20 can be connected to the nasal respiration assisting section 10, and therefore it is not necessary to attach a one-way valve for preventing gas leakage from occurring, to the tube 41 or the tube connecting coupler 26. Consequently, the production cost can be reduced.

Since the tubes 40, 41 are connected to the gas supplying portion 13 in the lateral directions, respectively, the respiration assistance device 1 can be easily located to the position where the device is to be attached to the human body H, by the tubes 40, 41.

After the bite block 20 is detached, the tube 41 can be connected to the gas supplying portion 13. In the respiration assistance device 1, therefore, the trouble of fixing the tube 41 which is detached from the bite block 20, to an adequate place can be reduced, and the convenience in the use can be improved.

Although, in the above-described embodiment, the respiration assistance device 1 has the gas sensor attaching portion 12 to which the gas sensor 30 is to be attached, the presently disclosed subject matter is not limited to this. Namely, the respiration assistance device may not include the gas sensor attaching portion.

Although the embodiment in which the respiration assistance device 1 includes the nasal respiration assisting section 10 and the bite block 20, and the nasal respiration assisting section 10 and the bite block 20 can be detached has been described, the presently disclosed subject matter is not limited to this. For example, the respiration assistance device of the presently disclosed subject matter may include only the nasal respiration assisting section 10. In this case, the respiration assistance device of the presently disclosed subject matter may be used independently, or may be used in combination with a bite block. The bite block which is used in combination with the respiration assistance device may be the bite block 20 which has been described above, or another bite block.

Although, in the respiration assistance device 1 of the above-described embodiment, the tube which is connected to the first tube connecting portion 133 is undetachable, and that which is connected to the second tube connecting portion 134 is detachable, the presently disclosed subject matter is not limited to this. In the respiration assistance device, for example, the tube which is connected to the second tube connecting portion 134 may be undetachable. In the presently disclosed subject matter, alternatively, both the tubes which are connected respectively to the first and second tube connecting portions 133, 134 may be detachable.

What is claimed is:

1. A respiration assistance device comprising:
   a nasal respiration assisting section for supplying a gas to a nasal cavity of a living body, and
   a bite block which is detachably attached to the nasal respiration assisting section, and which is configured to attach to an oral cavity of the living body,
   wherein the nasal respiration assisting section includes:
      a first gas supplying portion which is configured to supply the gas below one of nostrils of the living body,
      a second gas supplying portion which is configured to supply the gas below another nostril of the living body,
      a first tube connecting portion to which a tube for supplying the gas to the first gas supplying portion is connectable, and
      a second tube connecting portion to which a tube for supplying the gas to the second gas supplying portion is connectable,
   wherein each of the first gas supplying portion and the first tube connecting portion is formed at a body of the nasal respiration assisting section, and
   wherein the first gas supplying portion and the first tube connecting portion communicate with each other via a first gas path, and
   wherein the bite block includes:
      a wall surface portion which has an approximately tubular shape,
      an oral cavity contacting portion which is disposed on an outer surface of the wall surface portion, and which is configured to contact the oral cavity that is opened,
      a through hole which is disposed in an inner surface of the wall surface portion and into which a tubular article is insertable,
      a third gas supplying portion which is disposed in the through hole, and which is configured to supply gas to the oral cavity, and
      a third tube connecting portion to which a tube that supplies the gas to the third gas supplying portion is connectable, wherein in a front view, a line connecting the first tube connecting portion and the second tube connecting portion and a line connecting the third tube connecting portion and a center of the through hole are parallel.

2. The respiration assistance device according to claim 1, wherein one of the first tube connecting portion and the second tube connecting portion is undetachable from the corresponding tube, and another thereof is detachable from the corresponding tube.

3. The respiration assistance device according to claim 1, wherein,
   in a case where the bite block is attached, the tubes are connected to at least one of the first tube connecting portion and the second tube connecting portion, and the third tube connecting portion, respectively, and,
   in a case where the bite block is detached, the tubes are connected to the first tube connecting portion and the second tube connecting portion, respectively.

4. The respiration assistance device according to claim 1, further comprising:
   a first fitting portion which is disposed in the nasal respiration assisting section; and
   a second fitting portion which is disposed in the bite block, and which is fitted to the first fitting portion,
   wherein the first fitting portion and the second fitting portion enable the nasal respiration assisting section and the bite block to be detachably attached to each other.

5. The respiration assistance device according to claim 1, further comprising:
   an expiration collecting portion which is configured to collect an expiration introduced from the living body; and
   a gas sensor attaching portion which is disposed in the expiration collecting portion, and to which a gas sensor for measuring a concentration of a predetermined gas component contained in the expiration is attachable,
   wherein the nasal respiration assisting section includes a nasal cavity expiration introducing portion which is configured to connect to one of nostrils of the living body, and which is configured to introduce the expiration from the nasal cavity into the expiration collecting portion.

6. The respiration assistance device according to claim 1, further comprising:
   an expiration collecting portion which is configured to collect an expiration introduced from the living body; and
   a gas sensor attaching portion which is disposed in the expiration collecting portion, and to which a gas sensor for measuring a concentration of a predetermined gas component contained in the expiration is attachable,
   wherein the bite block includes:
      an oral cavity expiration introducing portion which is configured to introduce the expiration from the oral cavity into the expiration collecting portion.

7. The respiration assistance device according to claim 1, wherein each of the second gas supplying portion and the second tube connecting portion is formed at the body of the nasal respiration assisting section, and
   wherein the second gas supplying portion and the second tube connecting portion communicate with each other via a second gas path.

8. The respiration assistance device according to claim 7, wherein the first gas path and the second gas path are independent from each other.

\* \* \* \* \*